Oct. 13, 1964 R. KORDES Plant Pat. 2,449
ROSE PLANT
Filed Oct. 21, 1963
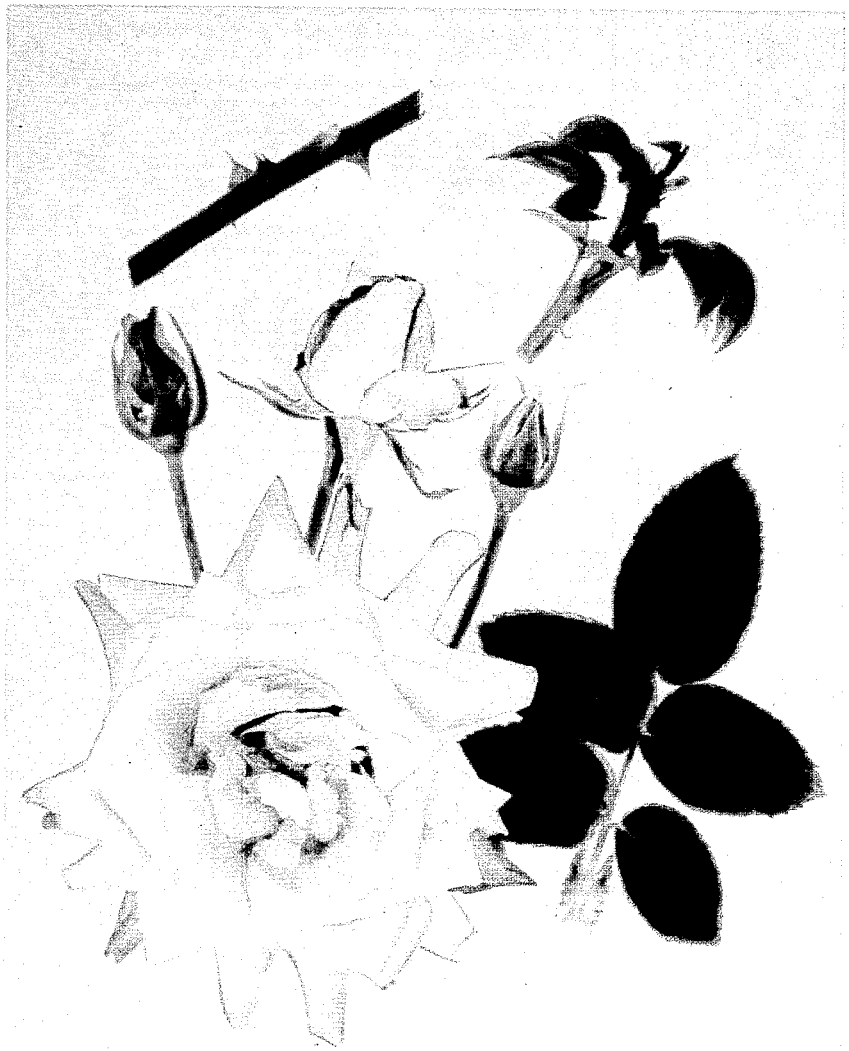
Inventor
Reimer Kordes
By: Robb & Robb
Attorneys United States Patent Office Plant Pat. 2,449
Patented Oct. 13, 1964

2,449
ROSE PLANT

Reimer Kordes, Barmstedt, near Elmshorn, Germany, assignor to Jackson & Perkins Company, Newark, N.Y., a corporation of New York Filed Oct. 21, 1963, Ser. No. 317,857
1 Claim. (Cl. Plt.—11)

The present invention relates to a new and distinct variety of rose plant of the hybrid tea class, which was originated by me by crossing an unnamed and unpatented self of the variety "Peace" (U.S. Plant Patent No. 591) with the variety "Kordes' Perfecta" (U.S. Plant Patent No. 1,604).

The primary objective of this breeding was to produce a new rose variety in which there is combined the excellent qualities of the antecedents "Peace" and "Kordes' Perfecta." This objective has been fully achieved as evidenced by the following unique combination of characteristics which are outstanding in the new variety and distinguish it from its parents, as well as from all other varieties of which I am aware:

(1) A very strong, vigorous and upright plant habit;

(2) Vigorous, rich and leathery dark green foliage;

(3) High-centered flowers which in many respects are similar to those of the parent variety "Kordes' Perfecta"; and (4) A distinctive and attractive general color tonality of the flowers corresponding to Begonia Rose, lightly overcast with Rose Red.

Asexual reproduction of the new variety by budding, as performed at Newark, New York, U.S.A., and also at Pleasanton, California, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—An unnamed "Peace" cross.
*Pollen parent.*—"Kordes' Perfecta."

Classification:
*Botanic.*—Hybrid tea.
*Commercial.*—Hybrid tea.

*Flower*

(Observations made from specimens grown outdoors at Newark, New York, U.S.A., in the early morning during the latter part of the month of August.)

Blooming habit: Recurrent—continuous.

Bud:
*Size.*—Very large.
*Form.*—Ovoid; is not affected by wet or hot weather.
*Color.*—When sepals first divide—Spinel Red, Plate 26. When petals begin to unfurl—Eugenia Red, Plate 13, lightly overcast with Spinel Red, Plate 26 on the edges of the petals. When half-blown: inside of petals—Rose Red, Plate 12, with lower half of petals very lightly overcast with Rose Color, Plate 12; reverse of petals—center of petals Cartridge Buff, Plate 30, with outer edges of petals Spectrum Red, Plate 1 and lightly overcast with Rose Red, Plate 12.
*Sepals.*—Slightly branched; curl back when petals begin to unfurl. Color: inside—Light Fluorite Green, Plate 32; outside—Chromium Green, Plate 32.
*Calyx.*—Color—Light Bice Green, Plate 17. Shape—apple. Size — large. Aspect — smooth. Odor when rubbed—none.
*Peduncle.* — Length — long. Aspect — rough. Strength—erect; heavy. Color—Russet, Plate 15.
*Opening.*—Opens up well; is not affected by adverse weather conditions.

Bloom:
*Size.*—Very large. Average size when fully expanded—from 4¾ inches to 5 inches.
*Borne.*—Both singly and several together.
*Stems.*—Long; strong.
*Form (when first open).*—High-centered. Permanence—retains its form to the end, but outer petals curl back.
*Petalage.*—Double (full but open center). Number of petals under normal conditions—45 to 50.
*Color.*—Center of flower—Rose Red, Plate 12, lightly overcast with Begonia Rose, Plate 1. Outer petals—Flesh Pink, Plate 13, with outer edge of petals Begonia Rose, Plate 1. Base of petals (aiglet)—Light Chalcedony Yellow, Plate 17. Inside of petals—Begonia Rose, Plate 1, lightly overcast with Rose Red, Plate 12. Reverse of petals—Rose Pink, Plate 12, lightly overcast with Deep Rose Pink, Plate 12. General tonality from a distance—Begonia Rose, Plate 1, very lightly overcast with Rose Red, Plate 12.
*Discoloration.*—General tonality at end of first day—Begonia Rose, Plate 1, overcast with Rose Red, Plate 12. Second day—Begonia Rose, Plate 1, overcast with Rose Red, Plate 12. Third day—Begonia Rose, Plate 1, lightly overcast with Rose Red, Plate 12.

Petals:
*Texture.*—Thick; is not affected by wet or hot weather.
*Appearance.*—Inside—shiny. Outside—satiny.
*Form.*—Oval.
*Arrangement.*—Imbricated (regularly arranged shingle-like).
*Petaloids in center.*—Many; large.
*Persistence.*—Drop off cleanly.
*Fragrance.*—Moderate. Nature—Old Rose perfume (centifolia).
*Lasting quality.* — On the plant — long. As cut flower—long.

*Genital Organs*

Stamens, anthers: Medium size; many; regularly arranged around styles. Color—Picric Yellow, Plate 4.
Stamens, filaments (threads): Medium length. Color—Sulphur Yellow, Plate 5.
Pollen: Color—Martius Yellow, Plate 4.
Styles: Bunched; uneven length; medium length; thin.
Stigmas: Color—Straw Yellow, Plate 16.
Ovaries: All enclosed in calyx.
Hips: None.
Seeds: None.

*Plant*

Form: Bush.
Growth: Vigorous; upright.
Foliage: Compound of 5–7 leaflets.
*Size.*—Very large.
*Quantity.*—Abundant.
*Color.*—New foliage: upper side—Yellowish Citrine, Plate 16, overcast with Van Dyke Red, Plate 13; under side—Water Green, Plate 41, overcast with Acajou Red, Plate 13. Old foliage: upper side—

Yew Green, Plate 31; under side—Rainette Green, Plate 31.

*Shape.*—Oval pointed.

*Texture.* — Upper side — leathery; glossy. Under side—smooth.

*Ribs and veins.*—Ordinary.

*Edge.*—Serrated (saw-toothed).

*Serration.*—Both double and single; small.

*Leaf stem.*—Color—Rainette Green, Plate 31. Under side—smooth.

*Stipules.*—Medium length; bearded.

Wood:

*New wood.*—Color—Light Bice Green, Plate 17. Bark—smooth.

*Old wood.*—Color—Cress Green, Plate 31. Bark—smooth.

Thorns:

*Thorns.*—Quantity: on main stalks from base—few; on laterals from stalk—few. Form—flat base; medium length; hooked downward. Color (when young)—Eugenia Red, Plate 13. Position—Irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a very strong, vigorous and upright plant habit, vigorous, rich and leathery dark green foliage, high-centered flowers which are similar in many respects to the flowers of the parent variety "Kordes' Perfecta" (U.S. Plant Patent No. 1,604), and a distinctive and attractive general color tonality of the flowers corresponding to Begonia Rose, lightly overcast with Rose Red.

No references cited.